US00PP22785P2

(12) United States Plant Patent
Smith

(10) Patent No.: US PP22,785 P2
(45) Date of Patent: Jun. 12, 2012

(54) ***CHRYSANTHEMUM* PLANT NAMED 'SYAUB ORAN'**

(50) Latin Name: *Chrysanthemum×morifolium*
Varietal Denomination: Syaub Oran

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/932,887

(22) Filed: Mar. 9, 2011

(51) Int. Cl.
*A01H 5/00* (2006.01)

(52) U.S. Cl. ..... Plt./290

(58) Field of Classification Search ..... Plt./290
See application file for complete search history.

*Primary Examiner* — Annette Para
(74) *Attorney, Agent, or Firm* — Joshua L. Price

(57) ABSTRACT

A new *Chrysanthemum* plant named 'Syaub Oran' particularly distinguished by the long-lasting, greyed-orange colored inflorescences, dark green foliage, with rounded and mounded plant habit.

1 Drawing Sheet

Latin name of the genus and species of the plant claimed: *Chrysanthemum×morifolium.*

Varietal denomination: 'Syaub Oran'.

BACKGROUND OF THE NEW PLANT

The present invention comprises a new *Chrysanthemum*, botanically known as *Chrysanthemum×morifolium*, and hereinafter referred to by the variety name 'Syaub Oran'.

'Syaub Oran' is a product of a planned breeding program. The new cultivar has long-lasting, greyed-orange colored inflorescences, dark green foliage, with rounded and mounded plant habit.

'Syaub Oran' originated from a hybridization made in February 2007 in a controlled breeding environment in Tenjo, Columbia. The female parent was the proprietary plant designated 'Yohannah', U.S. Plant Pat. No. 16,387, with lighter orange inflorescences, smaller plant habit that is a bit more upright, and a 1 week slower natural season flowering response.

The male parent of 'Syaub Oran' was identified as 'Yobonnie', U.S. Plant Pat. No. 18,886, with greyed-orange color that fades more quickly, a smaller plant size and a few days faster natural flowering response. The resultant seed was sown in June 2007.

'Syaub Oran' was selected as one flowering plant within the progeny of the stated cross in the November 2007 in a controlled environment in Alva, Fla.

The first act of asexual reproduction of 'Syaub Oran' was accomplished when vegetative cuttings were propagated from the initial selection in December 2007 in a controlled environment in Alva, Fla.

BRIEF SUMMARY OF INVENTION

Horticultural examination of plants grown from cuttings of the plant initiated in December 2007 and continuing thereafter has demonstrated that the combination of characteristics as herein disclosed for 'Syaub Oran' are firmly fixed and are retained through successive generations of asexual reproduction.

'Syaub Oran' has not been observed under all possible environmental conditions. The phenotype may vary significantly with variations in environment such as temperature, light intensity and day length.

A Plant Breeder's Right for this cultivar was applied for in Canada on Mar. 19, 2010 (No. 10-6889). 'Syaub Oran' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Syaub Oran' with colors being as true as possible with an illustration of this type.

The photographic drawing shows a flowering potted plant of the new variety.

DETAILED BOTANICAL DESCRIPTION

The plant used for the photographs was about 12 weeks old, grown in Monroeville, N.J., in an outdoor trial. One rooted cuttings grown in a nine inch pot with no terminal pinching of the apices. The photograph was taken in mid-September 2010 in New Jersey.

The plant descriptions and measurements were taken in Gilroy, Calif. in May 2010 under natural light. Plants were grown under conditions which approximate those generally used for potted *Chrysanthemum* trials in a greenhouse. These plants used in the descriptions were about 10 weeks old.

Color references are made to The Royal Horticultural Society Colour Chart (R.H.S.) 2001.

TABLE 1

DIFFERENCES BETWEEN THE NEW VARIETY 'SYAUB ORAN' AND A SIMILAR VARIETY

| | 'Syaub Oran' | 'Yogretchen' (U.S. Plant Pat. No. 13,672) |
|---|---|---|
| Flower color lastingness: | Lasts longer | Fades quicker |
| Growth habit: | Rounded/bit larger size | More upright/bit smaller size |
| Natural season response: | Few days slower | Few days faster |

Plant:

*Form, growth and habit*.—Herbaceous decorative garden-type, stems upright and outwardly spreading, freely branching, strong and moderately vigorous growth habit.

*Plant height*.—13-14 cm.

*Plant height* (*inflorescence included*).—20-24 cm.

*Plant width*.—20 cm.

*Garden performance and tolerance to weather*.—Very good.

Roots:

*Number of days to initiate roots*.—4 days at about 22 degrees C.

*Number of days to produce a rooted cutting*.—10-12 days at 22 degrees C.

*Type*.—Fine, fibrous, free branching.

*Color*.—RHS N155B but whiter.

Foliage:

*Arrangement*.—Alternate.

*Immature, leaf color, upper surface*.—RHS 147A.

*Lower surface*.—Closest to RHS 137C.

*Mature, leaf color, upper surface*.—RHS 147A.

*Lower surface*.—Closest to RHS 137C.

*Length*.—5.3-5.5 cm.

*Width*.—2.8-3.2 cm.

*Shape*.—Ovate.

*Base shape*.—Attenuate.

*Apex shape*.—Acute.

*Margin*.—Irregularly lobed; slightly palmate; serrate.

*Texture, upper surface*.—Bifid T-shaped hairs.

*Lower surface*.—Bifid T-shaped hairs.

*Color of veins, upper surface*.—RHS 138B.

*Color of veins, lower surface*.—RHS 138B.

*Petiole color*.—RHS 138B.

*Length*.—2.2-2.5 cm.

*Diameter*.—0.2 cm.

*Texture*.—Bifid T-shaped hairs.

Stem:

*Quantity of main branches per plant*.—4-6, with many secondary branches.

*Color of stem*.—RHS 146B.

*Length of stem*.—13-15 cm.

*Diameter*.—0.3-0.35 cm.

*Length of internodes*.—0.5-1.0 cm.

*Texture*.—Bifid T-shaped hairs.

*Color of peduncle*.—RHS 146B.

*Length of peduncle*.—5.7-7.0 cm.

*Peduncle diameter*.—0.15 cm.

*Texture*.—Bifid T-shaped hairs.

Inflorescence:

*Type*.—Compositae type, solitary decorative-type inflorescences, borne terminally above foliage, ray florets arranged acropetally on a capitulum.

*Quantity of short days to flowering* (*response time*).—54 days.

*Natural season flowering*.—Mid-September.

*Quantity of inflorescences per plant*.—Approximately 75.

*Lastingness of individual blooms on the plant*.—About 6 weeks from first flower.

*Fragrance*.—Slightly spicy.

Bud (just when opening/showing color):

*Color*.—Mottled hues of RHS 162D and RHS 164B.

*Length*.—1.0 cm.

*Width*.—0.8 cm.

*Shape*.—Oblate.

Immature inflorescence:

*Diameter*.—3.5 cm.

*Color of ray florets, upper surface*.—RHS 163B overlaid with RHS N163C and RHS N163B basally.

*Lower surface*.—RHS 163B with some overlay RHS 167C.

Mature inflorescence:

*Diameter*.—4.5-5.0 cm.

*Depth*.—2.0 cm.

*Total diameter of 'disc'*.—0.3-0.4 cm.

*Receptacle height*.—0.3 cm.

*Receptacle diameter*.—0.3-0.4 cm.

Ray florets:

*Average quantity of florets*.—Approximately 130 in numerous whorls.

*Color of florets, upper surface*.—RHS 163B overlaid RHS N163C and RHS N163B basally becoming more RHS 163C overlaid RHS 167B.

*Lower surface*.—Closest to RHS 163C.

*Length*.—2.3-2.6 cm.

*Width*.—0.6-0.7 cm.

*Shape*.—Elliptical.

*Apex shape*.—Irregularly emarginate.

*Margin*.—Entire.

*Texture, upper surface*.—Papillose.

*Lower surface*.—Papillose.

Disc florets:

*Average quantity of florets*.—Approximately 20-24.

*Color of florets*.—RHS 1C with RHS 12A apex.

*Length*.—0.5 cm.

*Width*.—0.1 cm.

*Shape*.—Tubular, elongated.

*Apex shape*.—Acute, 5 pointed.

Phyllaries:

*Quantity*.—Approximately 25.

*Color, upper surface*.—RHS 137A.

*Lower surface*.—RHS 137A but appears lighter with hairs.

*Length*.—0.6-0.7 cm.

*Width*.—0.2 cm.

*Shape*.—Ovate to ligulate.

*Apex shape*.—Acute.

*Based*.—Fused.

*Margins*.—Entire.

*Texture, upper surface*.—Smooth.

*Lower surface*.—Bifid T-shaped hairs.

Reproductive organs:

*Pistil*.—1.

*Length*.—0.5 cm.

*Style color*.—RHS 1B.

*Style length*.—0.3-0.4 cm.

*Stigma color*.—RHS 13A.

*Stigma shape*.—Bi-parted.
*Ovary color*.—Not observed.
*Stamens*.—1.
*Color of filaments*.—RHS 1C.
*Length filaments*.—0.3 cm.
*Anther color*.—RHS 13C.
*Anther length*.—0.1 cm.
*Anther shape*.—Oval
*Color of pollen*.—Not observed.
*Pollen amount*.—Not observed.
*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'Syaub Oran' substantially as illustrated and described herein.

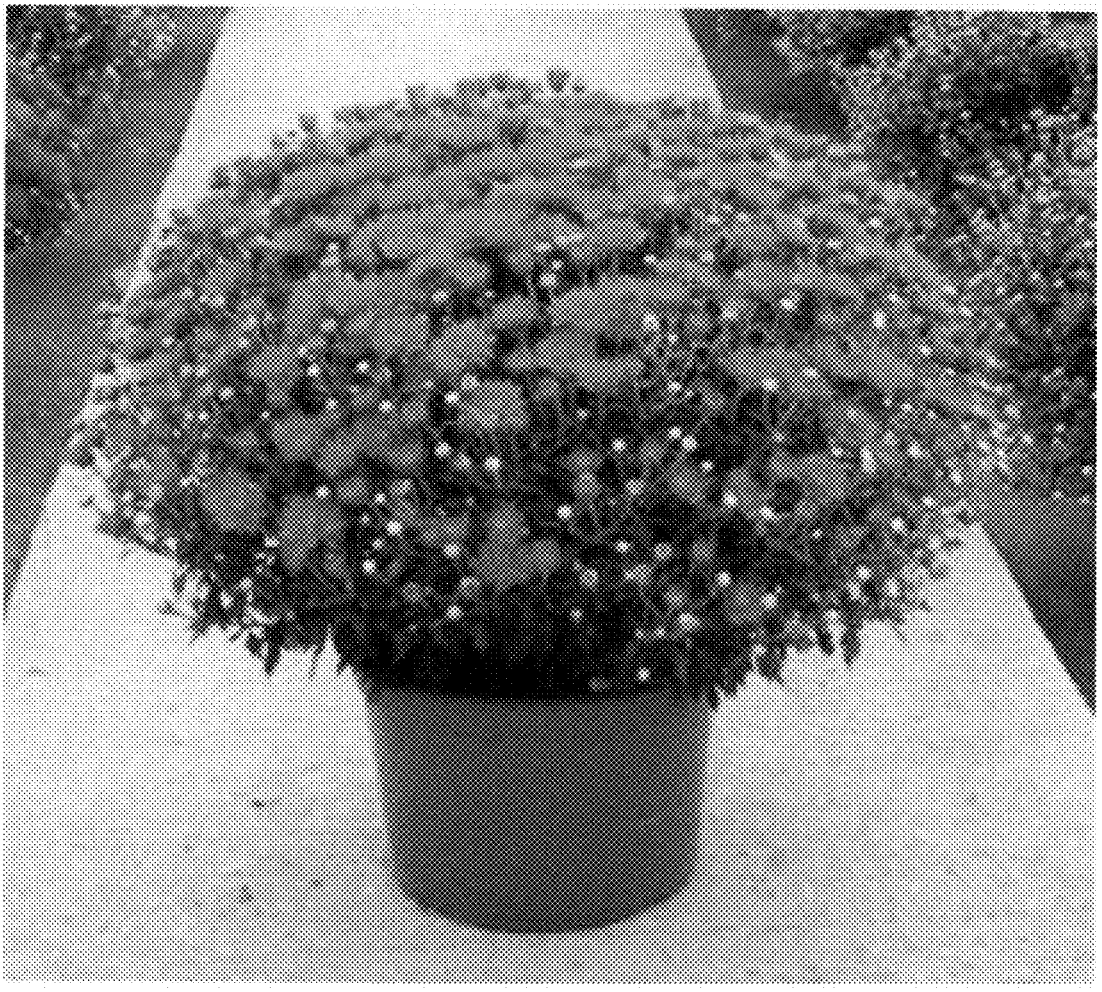

* * * * *